United States Patent
Su et al.

(10) Patent No.: US 9,034,654 B2
(45) Date of Patent: May 19, 2015

(54) METHOD FOR ANALYZING THE LIQUEFIED PETROLEUM GAS AND DEVICE THEREOF

(71) Applicant: INDUSTRIAL TECHNOLOGY RESEARCH INSTITUTE, Hsinchu (TW)

(72) Inventors: Hsiu-Li Su, Hsinchu (TW); Huan-Yi Hung, Changhua County (TW); Han-Wen Chu, Hsinchu (TW); Tsung-Chou Hsu, Changhua County (TW); Yao-Ting Huang, Tainan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 140 days.

(21) Appl. No.: 13/844,930

(22) Filed: Mar. 16, 2013

(65) Prior Publication Data

US 2014/0147927 A1  May 29, 2014

(30) Foreign Application Priority Data

Nov. 23, 2012   (TW) .............................. 101144035 A

(51) Int. Cl.
    *G01N 33/22*   (2006.01)

(52) U.S. Cl.
    CPC ........... *G01N 33/225* (2013.01); *Y10T 436/218* (2015.01)

(58) Field of Classification Search
    CPC .... G01N 33/22; G01N 33/225; Y10T 436/21; Y10T 436/214; Y10T 436/218
    USPC ............. 436/29, 60, 139, 141, 143, 161, 181; 422/54, 68.1, 82.13, 89, 93
    See application file for complete search history.

(56) References Cited

U.S. PATENT DOCUMENTS

| 6,000,274 A | 12/1999 | Lai et al. |
| 6,632,268 B2 | 10/2003 | Seeley |

(Continued)

FOREIGN PATENT DOCUMENTS

| CN | 1056706 A | 12/1991 |
| CN | 101092321 A | 12/2007 |

(Continued)

OTHER PUBLICATIONS

Intellectual Property Office, Ministry of Economic Affairs, R.O.C. "Office Action", Feb. 6, 2014, Taiwan.

(Continued)

*Primary Examiner* — Maureen Wallenhorst
(74) *Attorney, Agent, or Firm* — Tim Tingkang Xia, Esq.; Morris, Manning & Martin, LLP

(57) ABSTRACT

A method for analyzing the liquefied petroleum gas includes the following steps. Provide a sample of the liquefied petroleum gas, and one main component group of the liquefied petroleum gas includes at least one sub component group. Analyze the sample of the liquefied petroleum gas so as to obtain a first measured THC corresponding to the main component group and a second measured THC corresponding to the sub component group. Obtain a regressed THC according to the second measured THC and a predetermined relationship of THC. Obtain a result of THC according to the first measured THC, the regressed THC, and a predetermined range of THC. The predetermined range of THC corresponds to the main component group. The device for analyzing the liquefied petroleum gas includes an inlet, a multiposition valve, a first column, a second column, an analyzing apparatus, and a computing unit.

11 Claims, 6 Drawing Sheets

(56) References Cited

U.S. PATENT DOCUMENTS

| | | | |
|---|---|---|---|
| 7,981,680 | B2 | 7/2011 | Cummings |
| 2003/0216883 | A1 | 11/2003 | Lee |

FOREIGN PATENT DOCUMENTS

| | | | |
|---|---|---|---|
| CN | 102156172 | A | 8/2011 |
| CN | 102788856 | A | 11/2012 |
| JP | 2003343337 | A | 12/2003 |
| JP | 200560424 | A | 3/2005 |
| TW | 330240 | | 4/1998 |
| TW | 200724899 | | 7/2007 |
| TW | I285261 | B | 8/2007 |

OTHER PUBLICATIONS

Japan Patent Office, "Office Action", Feb. 6, 2014, Japan.
Standard Practice for Calculation of Certain Physical Properties of Liquefied Petroleum (LP) Gases From Compositional Analysis, An American National Standard, Designation: D 2598-02 (Reapproved 2007), Copyright: ASTM International.
Standard Test Method for Determination of Hydrocarbons in Liquefied Petroleum (LP) Gases and Propane/Propene Mixtures by Gas Chromatography, An American National Standard, Designation: D 2163-07, Copyright: ASTM International.
State Intellectual Property Office of the People's Republic of China, "Office Action", China, Jan. 28, 2015.

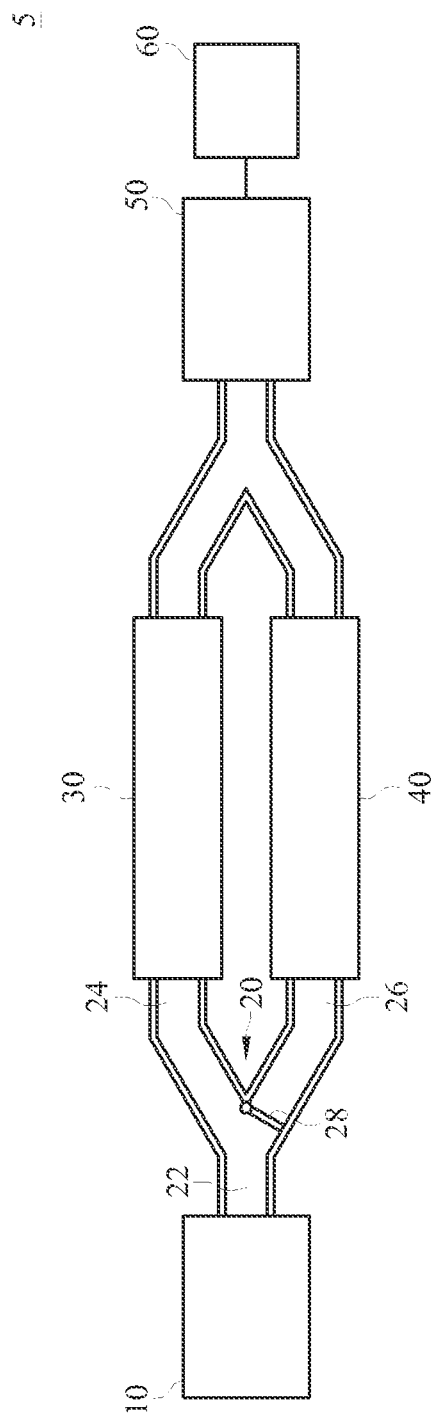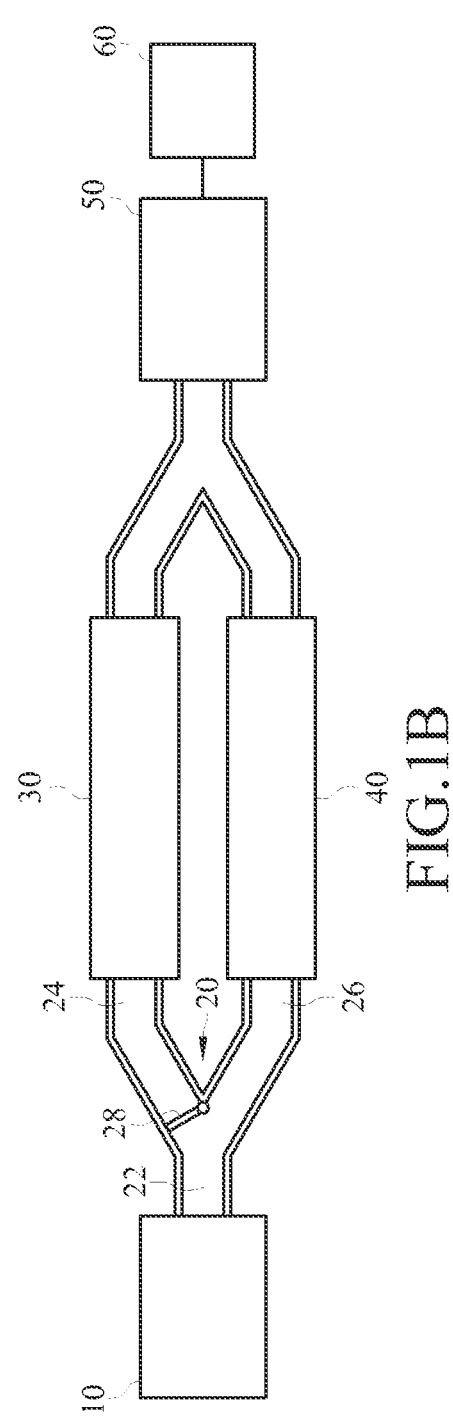

US 9,034,654 B2

METHOD FOR ANALYZING THE LIQUEFIED PETROLEUM GAS AND DEVICE THEREOF

CROSS-REFERENCE TO RELATED APPLICATIONS

This non-provisional application claims priority under 35 U.S.C. §119(a) on Patent Application No(s). 101144035 filed in Taiwan, R.O.C. on Nov. 23, 2012, the entire contents of which are hereby incorporated by reference.

TECHNICAL FIELD

The technical field relates to a method for analyzing and device thereof.

BACKGROUND

Liquefied petroleum gas, also called liquid petroleum gas, is the most important power source in life. Most of the liquefied petroleum gas is from the byproduct of refining crude oil. Also, some of the liquefied petroleum gas is from mixing propane and butane. The major component of the liquefied petroleum gas comprises alkanes and alkenes including 3 or 4 carbons. Liquefied petroleum gas is a gas at normal temperature and normal atmosphere, therefore, liquefied petroleum gas is usually supplied in pressurized steel vessels for transportation. Liquefied petroleum gas is widely used, from domestic use, business use, industry use, and fuels for transportations.

In order to protect the environment and the public safety, corresponding regulations and analysis are set up in different regions, as well as the quality of the liquefied petroleum gas is regulated and under control by corresponding liquefied petroleum gas laws.

Therefore, corresponding Offices need to examine the liquefied petroleum gas on the market. However, there are too many objects to be examined. If the samples of the liquefied petroleum gas are examined by all the examinations under the regulations, then each sample costs 2 to 3 days. Therefore, the cost of the examination is increased and it is hard for the Offices to examine all the objects.

Therefore, designers need to design a method for analyzing the liquefied petroleum gas.

SUMMARY

According to an embodiment, a method for analyzing the liquefied petroleum gas is disclosed. In the method, a sample of the liquefied petroleum gas is provided. One main group of the liquefied petroleum gas comprises at least one sub component group. Analyze the sample of the liquefied petroleum gas so as to obtain a first measured total hydrocarbon (THC) corresponding to the main component group and a second measured THC corresponding to the sub component group. Obtain a regressed THC according to the second measured THC and a predetermined relationship of THC. Obtain a result of THC according to the first measured THC, the regressed THC, and a predetermined range of THC. The predetermined rang of THC corresponds to the main component group.

According to an embodiment, a device for analyzing the liquefied petroleum gas is disclosed. The device comprises an inlet, a multiposition valve, a first column, a second column, an analyzing apparatus, and a computing unit. The inlet is adapted for receiving a sample of the liquefied petroleum gas. The multiposition valve comprises an inlet end, a first outlet end, and a second outlet end. The inlet connects to the inlet end. The first column connects to the first outlet end. The second column connects to the second outlet end. The second column includes different separation ability from the first column. The analyzing apparatus connects to the first column and the second column. The analyzing apparatus is adapted for exporting a regressed THC according to a first measured THC according to the second measured THC and obtaining an analyzing result of THC according to the first measured THC, the regressed THC, and a predetermined range of THC.

BRIEF DESCRIPTION OF THE DRAWINGS

The disclosure will become more fully understood from the detailed description given herein below for illustration only, and thus does not limit to the disclosure, and wherein:

FIG. 1A is a perspective view of a device for analyzing the liquefied petroleum gas according to an embodiment of the disclosure;

FIG. 1B is another perspective view of FIG. 1A;

DETAILED DESCRIPTION

Figure 2:
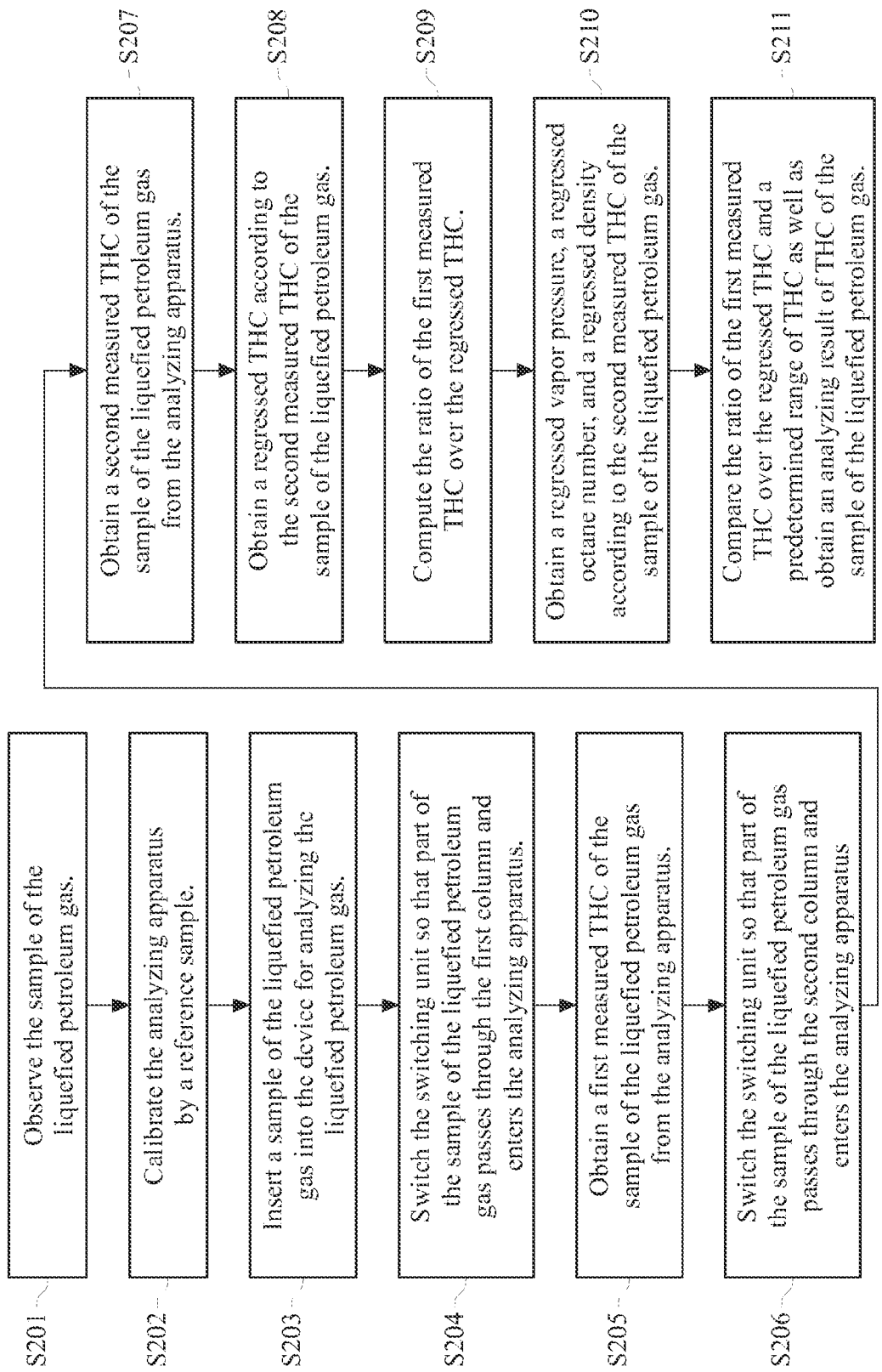
FIG. 2 is a flow chart of a method for analyzing the liquefied petroleum gas according to an embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

First, please refer to FIG. 1A and FIG. 1B. FIG. 1A is a perspective view of a device for analyzing the liquefied petroleum gas according to an embodiment of the disclosure. FIG. 1B is another perspective view of FIG. 1A. The device for analyzing the liquefied petroleum gas 5 comprises an inlet 10, a multiposition valve 20, a first column 30, a second column 40, an analyzing apparatus 50, and a computing unit 60. In this and some other embodiments, the combination of the inlet 10, the multiposition valve 20, the first column 30, the second column 40, and the analyzing apparatus 50 is a gas chromatography, but the disclosure is not limited thereto.

The inlet 10 is adapted for receiving a sample of the liquefied petroleum gas. The multiposition valve 20 comprises an inlet end 22, a first outlet end 24, and a second outlet end 26. The inlet end 22 connects to the inlet 10. In this and some other embodiments, the multiposition valve 20 further comprises a switching unit 28. Therefore, a user switches the switching unit 28 so that the inlet end 22 connects to the first outlet end 24 (FIG. 1A) or the inlet end 22 connects to the second outlet end 26 (FIG. 1B). Thereby, the user inserts the sample of the liquefied petroleum gas into the inlet 10, as well as the sample of the liquefied petroleum passes through the multiposition valve 20 and enters the first column 30 or the second column 40. Therefore, the sample of the liquefied petroleum gas is analyzed by the first column 30 or the second column 40.

The first column 30 connects to the first outlet end 24. In this and some other embodiments, the separation of compounds including low polarity, such as alkanes or alkenes, by the first column 30 is poor. In detail, the affinity between the stationary phase of the first column 30 and the components of the sample of the liquefied petroleum gas, such as alkanes or alkenes, is identical or similar. In other words, when the sample of the liquefied petroleum gas passes through the first column 30, the retention time of different components of the sample of the liquefied petroleum gas is identical or close. Therefore, the alkanes or alkenes of the components of the sample of the liquefied petroleum gas can not be separated.

The second column 40 connects to the second outlet end 26. The second column 40 includes different separation ability from the first column 30. In detail, the affinity between the stationary phase of the second column 40 and alkanes or alkenes is different from the affinity of the stationary phase of the first column 30. Therefore, when the sample of the liquefied petroleum gas passes through the second column 40, the retention time of the alkanes or alkenes of the components of the sample of the liquefied petroleum gas are different so that alkanes or alkenes of the components of the sample of the liquefied petroleum gas are separated.

The analyzing apparatus 50 connects to the first column 30 and the second column 40. In this and some other embodiments, the analyzing apparatus 50 is a flame ionization detector (FID). The analyzing apparatus 50 is adapted for analyzing the sample of the liquefied petroleum gas passing through the first column 30 or the second column 40. Also, the analyzing apparatus 50 is adapted for exporting a first measured THC corresponding to the sample of the liquefied petroleum gas entering the analyzing apparatus 50 after passing through the first column 30, as well as the analyzing apparatus 50 is adapted for exporting at least one second measured THC corresponding to the sub component group of the sample of the liquefied petroleum gas entering the analyzing apparatus 50 after passing through the second column 40.

The computing unit 60 is adapted for obtaining a regressed THC according to the second measured THC and obtaining an analyzing result of THC according to the first measured THC, the regressed THC, and a predetermined range of THC. The method for obtaining the analyzing result of THC according to the first measured THC, the regressed THC, and the predetermined range of THC is further described in the following paragraphs.

In this and some other embodiments, the computing unit 60 is also adapted for obtaining a regressed vapor pressure according to the second measured THC as well as obtaining an analyzing result of vapor pressure according to the regressed vapor pressure and a predetermined range of vapor pressure.

In this and some other embodiments, the computing unit 60 is also adapted for obtaining a regressed octane number according to the second measured THC as well as obtaining an analyzing result of octane number according to the regressed octane number and a predetermined range of octane number.

In this and some other embodiments, the computing unit 60 is also adapted for obtaining a regressed density according to the second measured THC as well as obtaining an analyzing result of density according to the regressed density and a predetermined range of density.

The method for obtaining the analyzing result of vapor pressure according to the regressed vapor pressure and the predetermined range of vapor pressure, obtaining the analyzing result of octane number according to the regressed octane number and the predetermined range of octane number, and obtaining the analyzing result of density according to the regressed density and the predetermined range of density are further described in the following paragraphs.

Then, please refer to FIG. 1A, FIG. 1B, and FIG. 2. FIG. 2 is a flow chart of a method for analyzing the liquefied petroleum gas according to an embodiment of the disclosure. The method for analyzing the liquefied petroleum gas comprises the following steps.

First, observe the sample of the liquefied petroleum gas (S201). When the sample of the liquefied petroleum gas comprises a liquid at normal temperature (e.g., 25° C.) and normal atmosphere (e.g., 1 atmosphere (atm)), the sample of the liquefied petroleum gas is an abnormal sample.

Then, calibrate the analyzing apparatus 50 by a reference sample (S202). The reference sample is, for example, propane (Air Products San Fu Co. Ltd: PR113053), butane (Air Products San Fu Co. Ltd: PR113055), or isobutane (Air Products San Fu Co. Ltd: PR113805).

Afterwards, insert a sample of the liquefied petroleum gas into the device for analyzing the liquefied petroleum gas 5 (S203). The sample of the liquefied petroleum gas is, for example, the liquefied petroleum gas for automobiles sold in a gas station. In this and some other embodiments, propane, butane, and isobutane are the analytes for analyzing the liquefied petroleum gas for automobiles sold in a gas station because propane, butane, and isobutane are the major components of the liquefied petroleum gas for automobiles. The main component group of the sample of the liquefied petroleum gas for automobiles comprises propane, butane, and isobutane, as well as propane, butane, and isobutane are the sub component groups of the sample of the liquefied petroleum gas for automobiles.

Then, switch the switching unit 28 so that part of the sample of the liquefied petroleum gas passes through the first column 30 and enters the analyzing apparatus 50 (S204). Since the separation of propane, butane, and isobutane by the first column 30 is poor, the retention time of propane, butane, and isobutane are identical or close. Therefore, the information obtained by the analyzing apparatus 50 corresponds to the mixture of propane, butane, and isobutane. That is, the main component group of the sample of the liquefied petroleum gas.

Afterwards, obtain a first measured THC of the sample of the liquefied petroleum gas from the analyzing apparatus 50 (S205). The first measured THC corresponds to the main component group of the sample of the liquefied petroleum gas. In other words, the THC of the major component of liquefied petroleum gas.

Then, switch the switching unit 28 so that part of the sample of the liquefied petroleum gas passes through the second column 40 and enters the analyzing apparatus 50 (S206). In this and some other embodiments, after switching the switching unit 28, the order that part of the sample of the liquefied petroleum gas passes through the first column 30 or the second column 40 is not to limit to the disclosure.

In this and some other embodiments, the second column 40 is HP-1(Product number: 19091Z-530, Agilent Technologies). The separation of the three sub component groups of the main component group of the sample of the liquefied petroleum gas, which are propane, butane, and isobutane, by the stationary phase of the second column 40 is greater. Therefore, the retention time of propane, butane, and isobutane is different. Thereby, a user is able to differentiate propane, butane, and isobutane of the sample of the liquefied petroleum gas.

Since the affinity between the stationary phase of the second column 40 and the three sub component groups of the main component group (propane, butane, and isobutane) of the sample of the liquefied petroleum gas is different, the retention time of the three sub component groups is different. Therefore, the three sub component groups are separated by the second column 40, and the analyzing apparatus 50 is able to analyze the three sub component groups respectively.

Afterwards, obtain a second measured THC of propane corresponding to propane of the sample of the liquefied petroleum gas, a second measured THC of butane corresponding to butane of the sample of the liquefied petroleum gas, and a second measured THC of isobutane corresponding to isobutane of the sample of the liquefied petroleum gas from the analyzing apparatus 50 (S207).

Then, obtain a regressed THC according to the second measured THC of propane, the second measured THC of butane, and the second measured THC of isobutane (S208). In detail, the regressed THC is obtained according to the second measured THC of propane, the second measured THC of butane, the second measured THC of isobutane, and a predetermined relationship of THC. Furthermore, the predetermined relationship of THC is a regression curve of the composition ratio of the sample of the liquefied petroleum gas and the regressed THC. The method for computing the regressed THC is as the formula 1, THC=−73.71x+101.82y+27372 (formula 1). THC presents the regressed THC, x presents the ratio of propane, and y presents the ratio of isobutane. The method for obtaining the regressed THC according to the ratio of propane and the ratio of isobutane as well as the method for obtaining the formula 1 are further described in the following paragraphs.

Afterwards, compute the ratio of the first measured THC over the regressed THC (S209).

Then, obtain a regressed vapor pressure, a regressed octane number, and a regressed density according to the second measured THC of propane of the sample of the liquefied petroleum gas, the second measured THC of butane of the sample of the liquefied petroleum gas, and the second measured THC of isobutane of the sample of the liquefied petroleum gas as well as a predetermined relationship of vapor pressure, a predetermined relationship of octane number, and a predetermined relationship of density (S210).

First, a summation of THC is obtained by adding the second measured THC of propane, the second measured THC of butane, and the second measured THC of isobutane. Then, the second measured THC of propane, the second measured THC of butane, and the second measured THC of isobutane are divided by the summation of THC respectively, as well as the ratio of propane, the ratio of butane, and the ratio of isobutane are obtained correspondingly. In this embodiment, the ratio of propane, the ratio of butane, and the ratio of isobutane present the corresponding ratio of gas volume of propane, the ratio of gas volume of butane, and the ratio of gas volume of isobutane. In some other embodiments, the ratio of propane, the ratio of butane, and the ratio of isobutane present the corresponding mole ratio of propane, the mole ratio of butane, and the mole ratio of isobutane.

The predetermined relationship of vapor pressure is a relationship between the composition ratio (e.g. ratio of gas volume, mole ratio) and the regressed vapor pressure. The formula for computing the regressed vapor pressure is: the regressed vapor pressure=(vp'×C)/100.

Wherein, vp' presents the vapor pressure of propane, butane, and isobutane at 40° C. (propane: 1353 kilopascal (kpa); butane: 376.9 kPa; isobutane: 531 kPa), and C presents the ratio of gas volume of propane, butane, and isobutane of the sample of the liquefied petroleum gas. 40° C. is the analyzing temperature according to a regulation for liquefied petroleum gas for automobiles.

The regressed vapor pressure of propane, the regressed vapor pressure of butane, and the regressed vapor pressure of isobutane are computed and summed so that the regressed vapor pressure of the sample of the liquefied petroleum gas at 40° C. is obtained.

The predetermined relationship of octane number is a relationship between the composition ratio (e.g. ratio of gas volume, mole ratio) and the regressed octane number. The formula for computing the regressed octane number is: the regressed octane number=(m×C)/100.

Wherein, m presents the octane number of propane, butane, and isobutane at 40° C. (propane: 95.6; butane: 88.9; isobutane: 97.1), and C presents the ratio of gas volume of propane, butane, and isobutane of the sample of the liquefied petroleum gas.

The regressed octane number of propane, the regressed octane number of butane, and the regressed octane number of isobutane are computed and summed so that the regressed octane number of the sample of the liquefied petroleum gas at 40° C. is obtained.

The predetermined relationship of density is a relationship between the composition ratio (e.g. ratio of gas volume, mole ratio) and the regressed density. The formula for computing the regressed density is: the regressed density=(sg'×C)/100.

Wherein, sg' presents the density of propane, butane, and isobutane at 15.6° C. (60° F.) (propane: 0.50736 gram/mililiter (g/mL); butane: 0.58407 g/mL; isobutane: 0.56293 g/mL), and C presents the ratio of gas volume of propane, butane, and isobutane of the sample of the liquefied petroleum gas.

The regressed density of propane, the regressed density of butane, and the regressed density of isobutane are computed and summed so that the regressed density of the sample of the liquefied petroleum gas is obtained.

Finally, compare the ratio of the first measured THC over the regressed THC and a predetermined range of THC as well as obtain an analyzing result of THC of the sample of the liquefied petroleum gas (S211). The predetermined range of hydrocarbon is the range of the ratio of the first measured THC over the regressed THC. When the ratio is in the range, then the sample of the liquefied petroleum gas is concerned to include a normal THC. When the ratio is over the range, then the sample of the liquefied petroleum gas is concerned to be an abnormal sample. In this embodiment, the predetermined range is between 97.76%~101.96%. Besides, when the samples of the liquefied petroleum gas further satisfies a predetermined range of vapor pressure(less than 1443.4 kPa), a predetermined range of octane number(greater than 92.5), and a predetermined range of density, then the sample of the liquefied petroleum gas is concerned to be a normal sample. When the regressed vapor pressure, the regressed octane number, or the regressed density is not in the predetermined ranges, then the sample of the liquefied petroleum gas is concerned to be an abnormal sample. Further analysis for the abnormal samples is required.

The method for obtaining the predetermined range of vapor pressure is as the followings. First, analyze standard samples by a method in the regulation and the method disclosed in the embodiment respectively. Compute the difference between the results obtained from the two methods, and obtain an average value and a standard deviation of the differences. Then, add the average value by 2 times of the standard deviation (56.6 kPa), and a limitation of the differences is determined. For example, when the regulation limits the vapor pressure of the liquefied petroleum gas for automobiles to be lower than 1500 kPa, then the predetermined range of vapor pressure in the method for analyzing the liquefied petroleum gas disclosed in the embodiment is lower than 1443.4 kPa (1500-56.6). The method for obtaining the predetermined range of octane number is similar to the method for obtaining the predetermined range of octane number. Standard samples are analyzed by a method in the regulation and the method disclosed in the embodiment respectively. The difference of the results obtained from the two methods is computed, and an average value and a standard deviation of the differences are obtained. The average value is added by 2 times of the standard deviation, and a limitation of the differences is determined. For example, when the regulation limits the octane number of the liquefied petroleum gas for automobiles to be greater than 89, then the predetermined range of octane number in the method for analyzing the liquefied petroleum gas disclosed in the embodiment is greater than 92.5(89+3.5). Also, the user can set up the predetermined range of density before the analysis.

Figure 3:
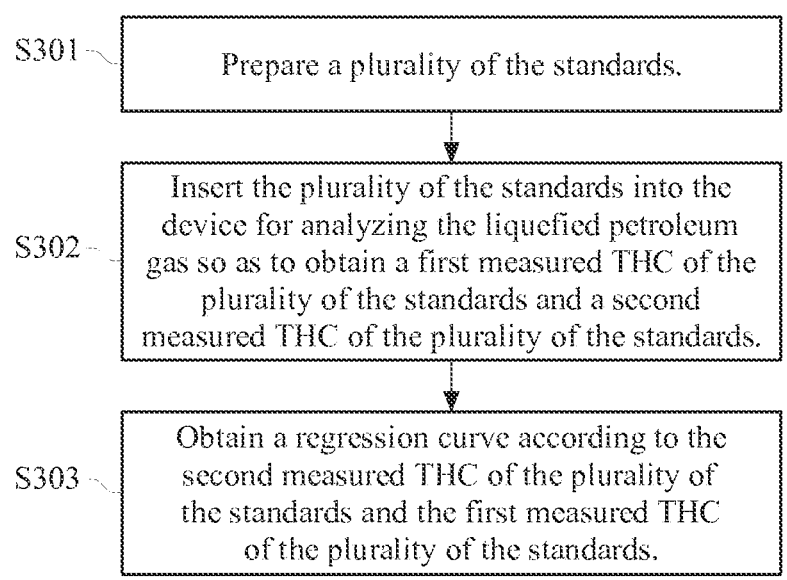
FIG. 3 is a flow chart of a method for creating a database of FIG. 2.
Figure 4:
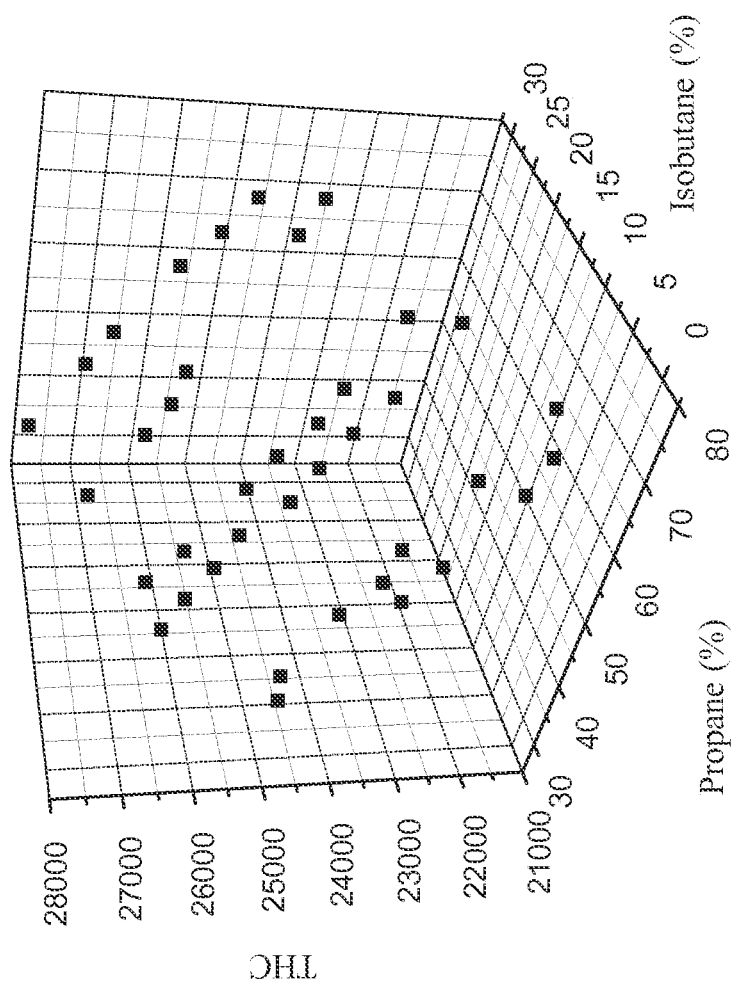
FIG. 4 is a 3D diagram according to a ratio of propane, a ratio of isobutane, and a first measured THC.

Please refer to FIG. 3 and FIG. 4. FIG. 3 is a flow chart of a method for creating a database of FIG. 2; FIG. 4 is a 3D diagram according to a ratio of propane, a ratio of isobutane, and a first measured THC.

First, prepare a plurality of the standards from propane (Air Products San Fu Co. Ltd: PR113053), butane (Air Products San Fu Co. Ltd: PR113055), and isobutane (Air Products San Fu Co. Ltd: PR113805)(S301). The ratio of propane, butane, and isobutane are different between the plurality of the standards.

Then, insert the plurality of the standards into the device for analyzing the liquefied petroleum gas so as to obtain a first measured THC of the plurality of the standards and a second measured THC of propane corresponding to propane of the plurality of the standards, a second measured THC of butane corresponding to butane of the plurality of the standards, and a second measured THC of isobutane corresponding to isobutane of the plurality of the standards (S302). The method for obtaining the first measured THC of the plurality of the standards, the second measured THC of propane of the plurality of the standards, the second measured THC of butane of the plurality of the standards, and the second measured THC of isobutane of the plurality of the standards is identical or similar to step S203 to step S207, so those steps are not described in this section.

Afterwards, obtain a regression curve according to the second measured THC of propane of the plurality of the standards, the second measured THC of butane of the plurality of the standards, the second measured THC of isobutane of the plurality of the standards, and the first measured THC of the plurality of the standards (S303).

In detail, a summation is obtained by adding the second measured THC of propane of the plurality of the standards, the second measured THC of butane of the plurality of the standards, and the second measured THC of isobutene of the plurality of the standards. The second measured THC of propane of the plurality of the standards, the second measured THC of butane of the plurality of the standards, and the second measured THC of isobutane of the plurality of the standards are divided by the summation respectively, as well as the ratio of propane, the ratio of butane, and the ratio of isobutane are obtained correspondingly.

Then, take the ratio of propane as the variable x, take the ratio of isobutene as the variable y, and take the first measured THC as the variable z so as to obtain the formula 1, the regression curve of the ratio of propane, the ratio of isobutene, and the first measured THC. $z(THC)=-73.71x+101.82y+27372$ (formula 1). 3D diagram according to a ratio of propane, a ratio of isobutane, and a first measured THC is as FIG. 4.

Thereby, a regression curve from the ratio of propane of the standards, the ratio of butane of the standards, and the ratio of isobutane of the standards is obtained. Therefore, when the ratio of propane and the ratio of isobutane of a sample are obtained, variable x and variable y are substituted by the ratio of propane of the sample and the ratio of isobutane of the sample, as well as a regressed THC of the sample is obtained.

Figure 5:
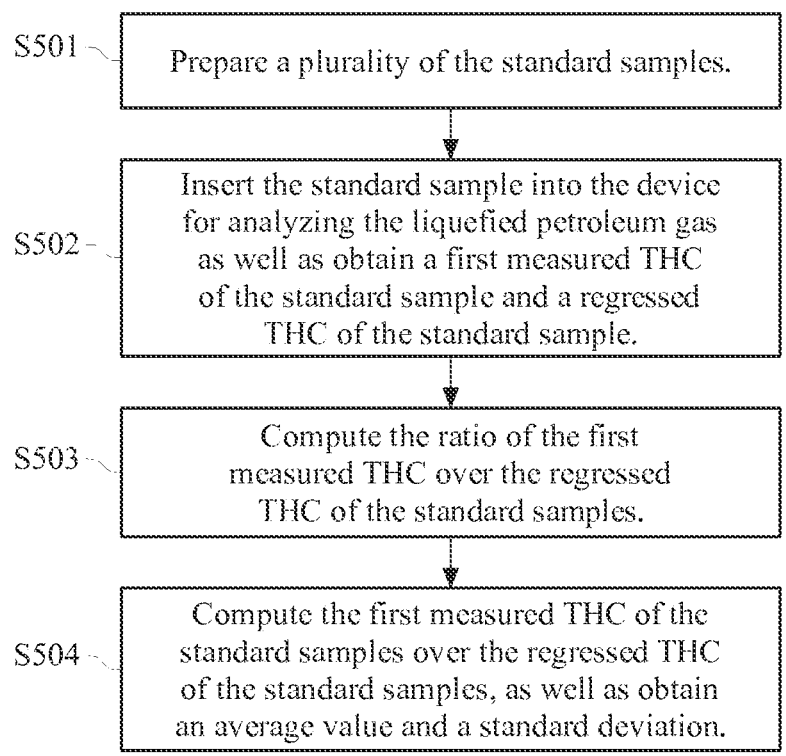
FIG. 5 is a flow chart of a method for creating a predetermined range of THC according to a regression curve of FIG. 3.

Please refer to FIG. 5 which is a flow chart of a method for creating a predetermined range of THC according to a regression curve of FIG. 3.

First, prepare a plurality of the standard samples from propane, butane, and isobutane (S501). The ratio of propane, butane, and isobutane are different between the plurality of the standard samples.

Then, insert the standard sample into the device for analyzing the liquefied petroleum gas as well as obtain a first measured THC of the standard sample and a regressed THC of the standard sample (S502). The method for obtaining the first measured THC of the standard samples and the regressed THC of the standard samples is identical or similar to step S203 to step S208, so those steps are not described in this section.

Afterwards, compute the ratio of the first measured THC over the regressed THC of the standard samples (S503).

Finally, compute the first measured THC of the standard samples over the regressed THC of the standard samples, as well as obtain an average value and a standard deviation (S504). In this embodiment, the ratio of the first measured THC over the regressed THC is between 97.76%~101.96%, the average is 99.86%, and the standard deviation is 1.05%. When the ratio of the first measured THC over the regressed THC is between the average+2× the standard deviation (99.86%+2×1.05%=101.96%) and the average−2× the standard deviation (99.86%−2×1.05%=97.76%), then the sample is a normal sample. Thereby, a database of the ratio of the first measured THC over the regressed THC is accomplished.

Please refer to Table 1, Table 1 is an analyzing result of the liquefied petroleum gas according to the method disclosed in the embodiments.

TABLE 1

The analyzing result of the method for analyzing the liquefied petroleum gas for automobiles

| sample | Propane (v/v, %) | Isobutene (v/v, %) | Butane (v/v, %) | Regressed THC | Measured THC | Ratio(%) (Measured THC/ Regressed THC) | Octane number | Vapor pressure | density |
|---|---|---|---|---|---|---|---|---|---|
| 1 | 68.23 | 12.57 | 19.20 | 23623 | 23463 | 99.32% | 94.40 | 1062 | 0.5248 |
| 2 | 70.96 | 11.63 | 17.41 | 23326 | 23420 | 100.40% | 94.50 | 1087 | 0.5233 |

TABLE 1-continued

The analyzing result of the method for analyzing the liquefied petroleum gas for automobiles

| sample | Propane (v/v, %) | Isobutene (v/v, %) | Butane (v/v, %) | Regressed THC | Measured THC | Ratio(%) (Measured THC/ Regressed THC) | Octane number | Vapor pressure | density |
|---|---|---|---|---|---|---|---|---|---|
| 3 | 68.49 | 12.73 | 18.78 | 23620 | 23320 | 98.73% | 94.43 | 1065 | 0.5246 |
| 4 | 68.9 | 12.27 | 18.83 | 23543 | 23329 | 99.09% | 94.42 | 1068 | 0.5245 |
| 5 | 71.02 | 11.69 | 17.28 | 23327 | 23473 | 100.62% | 94.49 | 1088 | 0.5231 |
| 6 | 70.66 | 11.83 | 17.51 | 23368 | 23519 | 100.65% | 94.49 | 1085 | 0.5234 |
| 7 | 68.55 | 12.49 | 18.96 | 23591 | 23403 | 99.20% | 94.41 | 1065 | 0.5246 |

Afterwards, please refer to Table 2, Table 2 is another analyzing result of the liquefied petroleum gas according to the method disclosed in the embodiments. In order to follow the regulation, abnormal samples need to be distinguished from normal samples by the method disclosed in the embodiments. In the following paragraphs, samples added with dimethyl ether are described as examples of abnormal samples.

For the samples added with dimethyl ether, the ratio of the measured THC over the regressed THC is over the range of 97.76%~101.96%. Thereby, the abnormal samples are distinguished from the normal samples.

TABLE 2

The analyzing result of the method for analyzing the liquefied petroleum gas for automobiles: abnormal samples (added with dimethyl ether)

| Dimethyl ether (%) | Propane (v/v, %) | Isobutene (v/v, %) | Butane (v/v, %) | Regressed THC | Measured THC | Ratio(%) (Measured THC/ Regressed THC) | Octane number | Vapor pressure | density |
|---|---|---|---|---|---|---|---|---|---|
| 1 | 68.88 | 12.92 | 18.20 | 23610 | 22249 | 94.23% | 94.47 | 1069 | 0.5242 |
| 2 | 68.77 | 12.95 | 18.28 | 23621 | 22138 | 93.72% | 94.46 | 1068 | 0.5242 |
| 3 | 68.78 | 12.94 | 18.28 | 23619 | 22033 | 93.28% | 94.46 | 1068 | 0.5242 |
| 4 | 68.88 | 12.91 | 18.20 | 23609 | 21897 | 92.75% | 94.46 | 1069 | 0.5241 |
| 5 | 68.79 | 12.93 | 18.27 | 23618 | 21860 | 92.56% | 94.45 | 1068 | 0.5242 |

In this embodiment, propane, butane, and isobutene are the analytes, but the disclosure is not limited thereto. In detail, species or quantities of the analytes may be adjusted according to the user need. For instance, in some other embodiments, propane and butane are the analytes. Besides, since the main component group of the liquefied petroleum gas for domestic use comprises the sub component group of C3 hydrocarbon (alkanes or alkenes including 3 carbons), the sub component group of C4 alkane (alkanes including 4 carbons), and the sub component group of C4 alkene (alkenes including 4 carbons), in another embodiment, C3 hydrocarbon, C4 alkane, and C4 alkene are the analytes for analyzing the liquefied petroleum gas for domestic use. The sub component group of C3 hydrocarbon comprises propane and propene. The sub component group of C4 alkane comprises butane and isobutane. The sub component group of C4 alkene comprises isobutene, 1-butene, cis-2-butene, trans-2-butene, and 1,3-butadiene. In the following descriptions, the method for analyzing the liquefied petroleum gas for domestic use is described.

First, observe the sample of the liquefied petroleum gas (S201). When the sample of the liquefied petroleum gas comprises a liquid at normal temperature and normal atmosphere, the sample of the liquefied petroleum gas is an abnormal sample.

Then, calibrate the analyzing apparatus 50 by a reference sample (S202). The reference sample is, for example, propane (Air Products San Fu Co. Ltd: PR113053), butane (Air Products San Fu Co. Ltd: PR113055), or trans-2-butene (Aldrich: 295086).

Afterwards, insert a sample of the liquefied petroleum gas into the device for analyzing the liquefied petroleum gas 5 (S203). Then, switch the switching unit 28 so that part of the sample of the liquefied petroleum gas passes through the first column 30 and enters the analyzing apparatus 50 (S204). Since the separation of C3 hydrocarbon, C4 alkane, and C4 alkene by the first column 30 is poor, the retention time of C3 hydrocarbon, C4 alkane, and C4 alkene are identical or close. Therefore, the information obtained by the analyzing apparatus 50 corresponds to the mixture of C3 hydrocarbon, C4 alkane, and C4 alkene. That is, the main component group of the sample of the liquefied petroleum gas.

Afterwards, obtain a first measured THC of the sample of the liquefied petroleum gas from the analyzing apparatus 50 (S205). The first measured THC corresponds to the main component group of the sample of the liquefied petroleum gas. In other words, the THC of the major component of liquefied petroleum gas.

Then, switch the switching unit 28 so that part of the sample of the liquefied petroleum gas passes through the second column 40 and enters the analyzing apparatus 50 (S206). In this and some other embodiments, the order of switching the switching unit 28 so that part of the sample of the liquefied petroleum gas passes through the first column and the second column is not to limit to the disclosure.

In this and some other embodiments, the second column 40 is HP-1(Product number: 19091Z-530, Agilent Technologies). The separation of the three sub component groups of the main component group of the sample of the liquefied petroleum gas, which are C3 hydrocarbon, C4 alkane, and C4 alkene, by the stationary phase of the second column 40 is greater. Therefore, the retention time of C3 hydrocarbon, C4 alkane, and C4 alkene is different. Thereby, a user is able to differentiate C3 hydrocarbon, C4 alkane, and C4 alkene of the sample of the liquefied petroleum gas.

Since the affinity between the stationary phase of the second column 40 and the three sub component groups of the main component group (C3 hydrocarbon, C4 alkane, and C4 alkene) of the sample of the liquefied petroleum gas is different, the retention time of the three sub component groups is different. Therefore, the three sub component groups are separated by the second column 40, and the analyzing apparatus 50 is able to analyze the three sub component groups respectively.

Afterwards, obtain a second measured THC of C3 hydrocarbon corresponding to C3 hydrocarbon of the sample of the liquefied petroleum gas, a second measured THC of C4 alkane corresponding to C4 alkane of the sample of the liquefied petroleum gas, and a second measured THC of C4 alkene corresponding to C4 alkene of the sample of the liquefied petroleum gas from the analyzing apparatus 50 (S207).

Then, obtain a regressed THC according to the second measured THC of C3 hydrocarbon, the second measured THC of C4 alkane, and the second measured THC of C4 alkene (S208). In detail, the regressed THC is obtained according to the second measured THC of C3 hydrocarbon, the second measured THC of C4 alkane, the second measured THC of C4 alkene, and a predetermined relationship of THC. Furthermore, the predetermined relationship of THC is a regression curve of the composition ratio and the regressed THC. The method for computing the regressed THC is as the formula 2, THC=−151.65x−76.63y+53217 (formula 2). THC presents the regressed THC, x presents the ratio of C3 hydrocarbon, and y presents the ratio of C4 alkene. The method for obtaining the regressed THC according to the ratio of C3 hydrocarbon and the ratio of C4 alkene as well as the method for obtaining the formula 2 are further described in the following paragraphs.

Afterwards, compute the ratio of the first measured THC over the regressed THC (S209).

Then, obtain a regressed vapor pressure and a regressed density according to the second measured THC of C3 hydrocarbon of the sample of the liquefied petroleum gas, the second measured THC of C4 alkane of the sample of the liquefied petroleum gas, and the second measured THC of C4 alkene of the sample of the liquefied petroleum gas as well as a predetermined relationship of vapor pressure and a predetermined relationship of density (S210). Since the liquefied petroleum gas for domestic use is different from the liquefied petroleum gas for automobiles, the extent of engine knocking is not concerned by the user. Therefore, the octane number is not examined in the regulation. However, when the user set up a predetermined range of octane of the standard sample, analysis for the octane number of the liquefied petroleum gas for domestic use is also available.

First, a summation of THC is obtained by adding the second measured THC of C3 hydrocarbon, the second measured THC of C4 alkane, and the second measured THC of C4 alkene. Then, the second measured THC of C3 hydrocarbon, the second measured THC of C4 alkane, and the second measured THC of C4 alkene are divided by the summation of THC respectively, as well as the ratio of C3 hydrocarbon, the ratio of C4 alkane, and the ratio of C4 alkene are obtained correspondingly. In this embodiment, the ratio of C3 hydrocarbon, the ratio of C4 alkane, and the ratio of C4 alkene present the corresponding ratio of gas volume of C3 hydrocarbon, the ratio of gas volume of C4 alkane, and the ratio of gas volume of C4 alkene. In some other embodiments, the ratio of C3 hydrocarbon, the ratio of C4 alkane, and the ratio of C4 alkene present the corresponding mole ratio of C3 hydrocarbon, the mole ratio of C4 alkane, and the mole ratio of C4 alkene.

The predetermined relationship of vapor pressure is a relationship between the composition ratio (e.g. ratio of gas volume, mole ratio) and the regressed vapor pressure. The formula for computing the regressed vapor pressure is: the regressed vapor pressure=(vp'×C)/100.

Wherein, vp' presents the vapor pressure of C3 hydrocarbon, C4 alkane, and C4 alkene at 37.8° C. (C3 hydrocarbon: 1317 kpa; C4 alkane: 431 kPa; C4 alkene: 380 kPa), and C presents the ratio of gas volume of C3 hydrocarbon, C4 alkane, and C4 alkene of the sample of the liquefied petroleum gas. 37.8° C. is the analyzing temperature according to a regulation for liquefied petroleum gas for domestic use.

In detail, the vapor pressure of propane is 1317 kPa, the vapor pressure of propene is 1570 kPa, the vapor pressure of butane is 355 kPa, the vapor pressure of isobutane is 507 kPa, the vapor pressure of 1-butene is 415 kPa, the vapor pressure of isobutene is 426 kPa, the vapor pressure of cis-2-butene is 314 kPa, the vapor pressure of teans-2-butene is 340 kPa, and the vapor pressure of 1,3-butadiene is 405 kPa. Since propane is the major component of the sub component group of C3 hydrocarbon of the liquefied petroleum gas for domestic use, the vapor pressure of C3 hydrocarbon is calculated as the vapor pressure of propane. Since the ratios of butane and isobutane are close in the sub component group of C4 alkane, the vapor pressure of C4 alkane is calculated as the average of the vapor pressure of butane and the vapor pressure of isobutane. Since the ratios of the 5 alkenes are close in the sub component group of C4 alkene, the vapor pressure of C4 alkene is calculated as the average of the vapor pressure of the 5 alkenes.

The regressed vapor pressure of C3 hydrocarbon, the regressed vapor pressure of C4 alkane, and the regressed vapor pressure of C4 alkene are computed and summed so that the regressed vapor pressure of the sample of the liquefied petroleum gas at 37.8° C. is obtained.

The predetermined relationship of density is a relationship between the composition ratio (e.g. ratio of gas volume, mole ratio) and the regressed density. The formula for computing the regressed density is: the regressed density=(sg'×C)/100.

Wherein, sg' presents the density of C3 hydrocarbon, C4 alkane, and C4 alkene at 15.6° C. (60° F.) (C3 hydrocarbon: 0.5074g/mL; C4 alkane: 0.5735g/mL; C4 alkene: 0.6138 g/mL), and C presents the ratio of gas volume of C3 hydrocarbon, C4 alkane, and C4 alkene of the sample of the liquefied petroleum gas.

In detail, the density of propane is 0.50736 g/mL, the density of propene is 0.52264 g/mL, the density of butane is 0.58407 g/mL, the density of isobutane is 0.56293 g/mL, the density of 1-butene is 0.60035 g/mL, the density of isobutene is 0.60153 g/mL, the density of cis-2-butene is 0.62858 g/mL, the density of trans-2-butene is 0.61116 g/mL, and the density of 1,3-butadiene is 0.62722 g/mL. Since propane is the major component of the sub component group of C3 hydrocarbon of the liquefied petroleum gas for domestic use, the density of C3 hydrocarbon is calculated as the density of propane. Since the ratios of butane and isobutane are close in the sub component group of C4 alkane, the density of C4 alkane is calculated as the average of the density of butane and the density of isobutane. Since the ratios of the 5 alkenes are close in the sub component group of C4 alkene, the density of C4 alkene is calculated as the average of the density of the 5 alkenes.

The regressed density of C3 hydrocarbon, the regressed density of C4 alkane, and the regressed density of C4 alkene are computed and summed so that the regressed density of the sample of the liquefied petroleum gas is obtained.

Finally, compare the ratio of the first measured THC over the regressed THC and a predetermined range of THC as well as obtain an analyzing result of THC of the sample of the liquefied petroleum gas (S211). The predetermined range of hydrocarbon is the range of the ratio of the first measured THC over the regressed THC. When the ratio is in the range, then the sample of the liquefied petroleum gas is concerned to include a normal THC. When the ratio is over the range, then the sample of the liquefied petroleum gas is concerned to be an abnormal sample. In this embodiment, the predetermined range is between 98.40%~101.88%. Besides, when the samples of the liquefied petroleum gas further satisfies a predetermined range of vapor pressure(less than 1370.9 kPa) and a predetermined range of density, then the sample of the liquefied petroleum gas is concerned to be a normal sample. When the regressed vapor pressure or the regressed density is not in the predetermined ranges, then the sample of the liquefied petroleum gas is concerned to be an abnormal sample. Further analysis for the samples is required.

The method for obtaining the predetermined range of vapor pressure is as the followings. First, analyze standard samples by a method in the regulation and the method disclosed in the embodiment respectively. Compute the difference between the results obtained from the two methods, and obtain an average value and a standard deviation of the differences. Then, add the average value by 2 times of the standard deviation (63.1 kPa), and a limitation of the differences is determined. For example, when the regulation limits the vapor pressure of the liquefied petroleum gas for domestic use to be lower than 1434 kPa, then the predetermined range of vapor pressure in the method for analyzing the liquefied petroleum gas disclosed in the embodiment is lower than 1370.9 kPa (1434-63.1). Also, the user can set up the predetermined range of density before the analysis.

Figure 6:
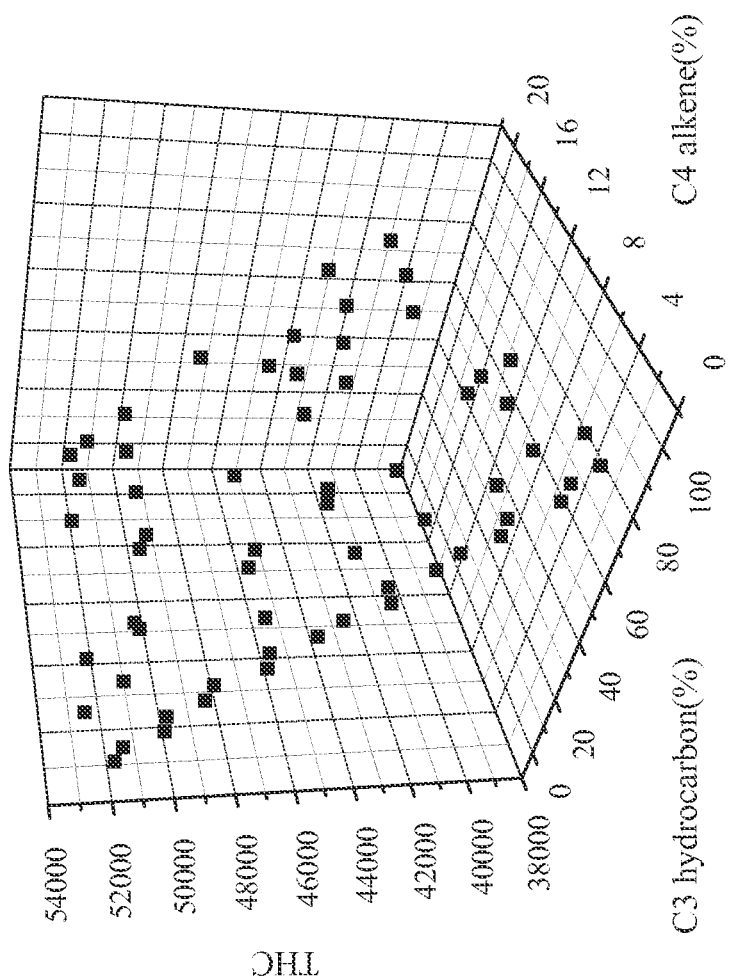
FIG. 6 is a 3D diagram according to a ratio of C3 hydrocarbon, a ratio of C4 alkene, and a first measured THC.

Please refer to FIG. 3 and FIG. 6. FIG. 6 is a 3D diagram according to a ratio of C3 hydrocarbon, a ratio of C4 alkene, and a first measured THC.

First, prepare a plurality of the standards from propane (Air Products San Fu Co. Ltd: PR113053), butane (Air Products San Fu Co. Ltd: PR113055), and trans-2-butene (Aldrich: 295086)(S301). The ratio of propane, butane, and trans-2-butene are different between the plurality of the standards.

Then, insert the plurality of the standards into the device for analyzing the liquefied petroleum gas so as to obtain a first measured THC of the plurality of the standards and a second measured THC of C3 hydrocarbon corresponding to C3 hydrocarbon of the plurality of the standards, a second measured THC of C4 alkane corresponding to C4 alkane of the plurality of the standards, and a second measured THC of C4 alkene corresponding to C4 alkene of the plurality of the standards (S302). The method for obtaining the first measured THC of the plurality of the standards, the second measured THC of C3 hydrocarbon of the plurality of the standards, the second measured THC of C4 alkane of the plurality of the standards, and the second measured THC of C4 alkene of the plurality of the standards is identical or similar to step S203 to step S207, so those steps are not described in this section.

Afterwards, obtain a regression curve according to the second measured THC of C3 hydrocarbon of the plurality of the standards, the second measured THC of C4 alkane of the plurality of the standards, the second measured THC of C4 alkene of the plurality of the standards, and the first measured THC of the plurality of the standards (S303).

In detail, a summation is obtained by adding the second measured THC of C3 hydrocarbon of the plurality of the standards, the second measured THC of C4 alkane of the plurality of the standards, and the second measured THC of C4 alkene of the plurality of the standards. The second measured THC of C3 hydrocarbon of the plurality of the standards, the second measured THC of C4 alkane of the plurality of the standards, and the second measured THC of C4 alkene of the plurality of the standards are divided by the summation respectively, as well as the ratio of C3 hydrocarbon, the ratio of C4 alkane, and the ratio of C4 alkene are obtained correspondingly.

Then, take the ratio of C3 hydrocarbon as the variable x, take the ratio of C4 alkene as the variable y, and take the first measured THC as the variable z so as to obtain the formula 2, the regression curve of the ratio of C3 hydrocarbon, the ratio of C4 alkene, and the first measured THC. $z(THC)=-151.65x-76.63y+53217$ (formula 2). 3D diagram according to a ratio of C3 hydrocarbon, a ratio of C4 alkene, and a first measured THC is as FIG. 6.

Thereby, a regression curve from the ratio of C3 hydrocarbon of the standards, the ratio of C4 alkane of the standards, and the ratio of C4 alkene of the standards is obtained. Therefore, when the ratio of C3 hydrocarbon and the ratio of C4 alkene of a sample are obtained, variable x and variable y are substituted by the ratio of C3 hydrocarbon of the sample and the ratio of C4 alkene of the sample, as well as a regressed THC of the sample is obtained.

Please refer to FIG. 5 again. First, prepare a plurality of the standard samples from C3 hydrocarbon, C4 alkane, and C4 alkene (S501). The ratio of C3 hydrocarbon, C4 alkane, and C4 alkene are different between the plurality of the standard samples.

Then, insert the standard sample into the device for analyzing the liquefied petroleum gas as well as obtain a first measured THC of the standard sample and a regressed THC of the standard sample (S502). The method for obtaining the first measured THC of the standard samples and the regressed THC of the standard samples is identical or similar to step S203 to step S208, so those steps are not described in this section.

Afterwards, compute the ratio of the first measured THC over the regressed THC of the standard samples (S503).

Finally, compute the first measured THC of the standard samples and the regressed THC of the standard samples, as well as obtain an average value and a standard deviation (S504). In this embodiment, the average of the ratio of the first measured THC over the regressed THC is 100.14%, and the standard deviation is 0.87%. When the ratio of the first measured THC over the regressed THC is between the average+ 2× the standard deviation (100.14%+2×0.87%=101.88%) and the average−2× the standard deviation (100.14%−2×0.87%=98.40%), then the sample is a normal sample. Thereby, a database of the ratio of the first measured THC over the regressed THC is accomplished. Please refer to Table 3, Table 3 is an analyzing result of the liquefied petroleum gas for domestic use according to the method disclosed in the embodiments.

TABLE 3

The analyzing result of the method for analyzing the liquefied petroleum gas for domestic use

| sample | C3 hydrocarbon (v/v, %) | C4 alkane (v/v, %) | C4 alkene (v/v, %) | Regressed THC | Measured THC | Ratio(%) (Measured THC/ Regressed THC) | Vapor pressure | density |
|---|---|---|---|---|---|---|---|---|
| 1 | 42.30 | 41.80 | 15.89 | 45954 | 45584 | 100.81 | 797.7 | 0.5519 |
| 2 | 43.94 | 40.87 | 15.18 | 45575 | 45389 | 100.41 | 812.6 | 0.5506 |
| 3 | 40.37 | 43.34 | 16.29 | 46263 | 45847 | 100.91 | 780.3 | 0.5534 |

TABLE 3-continued

The analyzing result of the method for analyzing the liquefied petroleum gas for domestic use

| sample | C3 hydrocarbon (v/v, %) | C4 alkane (v/v, %) | C4 alkene (v/v, %) | Regressed THC | Measured THC | Ratio(%) (Measured THC/ Regressed THC) | Vapor pressure | density |
|---|---|---|---|---|---|---|---|---|
| 4 | 45.50 | 54.27 | 0.23 | 46851 | 46299 | 101.19 | 834.0 | 0.5435 |
| 5 | 44.30 | 45.30 | 10.40 | 45331 | 45702 | 99.19 | 818.2 | 0.5484 |
| 6 | 45.80 | 39.62 | 14.58 | 45040 | 45154 | 99.75 | 829.4 | 0.5491 |
| 7 | 37.88 | 45.14 | 16.98 | 46127 | 46171 | 99.90 | 757.9 | 0.5553 |

According to the method for analyzing the liquefied petroleum gas and the device thereof disclosed by the disclosure, a predetermined range of hydrocarbon is set up before analysis. Therefore, the user only needs to analyze the first measured THC of the sample of the liquefied petroleum gas and the second measured THC of the sub component groups by the device for analyzing the liquefied petroleum gas (e.g. gas chromatography) so as to analyze the sample of the liquefied petroleum gas. Thereby, the analysis becomes faster. Besides, the regressed vapor pressure, the regressed octane number, and the regressed density of the sample of the liquefied petroleum gas are obtained by computing the second measured THC of the sample of the liquefied petroleum gas and the predetermined range of vapor pressure, the predetermined range of octane number, and the predetermined range of density. Therefore, the analysis covers multiple examinations. Besides, after abundant and quick preliminary analysis of all the samples of the liquefied petroleum gas according to the method for analyzing the liquefied petroleum gas and the device thereof, then abnormal samples are examined by analysis with full specifications.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for analyzing a liquefied petroleum gas, comprising:
providing a predetermined relationship of total hydrocarbon and a predetermined range of total hydrocarbon, the predetermined relationship of total hydrocarbon and the predetermined range of total hydrocarbon are based on regression analysis of total hydrocarbon of a plurality of reference samples of the liquefied petroleum gas;
providing a sample of the liquefied petroleum gas, wherein the sample of the liquefied petroleum gas comprises a main component group, and the main component group comprises a plurality of sub component groups;
analyzing the sample of the liquefied petroleum gas so as to obtain a first measured total hydrocarbon corresponding to the main component group and a second measured total hydrocarbon corresponding to one of the plurality of sub component groups;
obtaining a regressed total hydrocarbon according to the second measured total hydrocarbon and the predetermined relationship of total hydrocarbon; and
obtaining an analyzing result of total hydrocarbon according to the first measured total hydrocarbon, the regressed total hydrocarbon, and the predetermined range of total hydrocarbon;
wherein, the predetermined relationship of total hydrocarbon is a function of regression analysis, a plurality of variables in the function of regression analysis represent ratios of the second measured total hydrocarbon of one of the plurality of sub component groups to a summation of all the second measured total hydrocarbon of the plurality of sub component groups, and the regressed total hydrocarbon is an unknown number of the function of regression analysis, and the predetermined range of total hydrocarbon is a range of a ratio of the first measured total hydrocarbon to the regressed total hydrocarbon.

2. The method for analyzing the liquefied petroleum gas as claimed in claim 1, further comprising:
providing a predetermined range of vapor pressure, the predetermined range of vapor pressure is based on a predetermined relationship of vapor pressure of the plurality of reference samples of the liquefied petroleum gas, the predetermined relationship of vapor pressure satisfies following condition:
a regressed sub vapor pressure=(vp'×C)/100,
where vp' represents a vapor pressure of the plurality of sub component groups, C represents a volume percent of the plurality of sub component groups;
obtaining a regressed vapor pressure according to the second measured total hydrocarbon and the predetermined relationship of vapor pressure, and the regressed vapor pressure being summation of regressed sub vapor pressures; and
obtaining an analyzing result of vapor pressure according to the regressed vapor pressure and the predetermined range of vapor pressure.

3. The method for analyzing the liquefied petroleum gas as claimed in claim 1, further comprising:
providing a predetermined range of octane number, the predetermined range of octane number is based on a predetermined relationship of octane number of the plurality of reference samples of the liquefied petroleum gas, the predetermined relationship of octane number satisfies following condition:
a regressed sub octane number=(m×C)/100,
where m represents an octane number of the plurality of sub component groups, C represents a volume percent of the plurality of sub component groups;
obtaining a regressed octane number according to the second measured total hydrocarbon and the predetermined relationship of octane number, the regressed octane number being summation of regressed sub octane numbers; and
obtaining an analyzing result of octane number according to the regressed octane number and the predetermined range of octane number.

4. The method for analyzing the liquefied petroleum gas as claimed in claim 1, further comprising:
providing a predetermined range of density, the predetermined range of density is based on a predetermined relationship of density of the plurality of reference samples of the liquefied petroleum gas, the predetermined relationship of density satisfies following condition:

a regressed sub density=(sg'×C)/100, where sg' represents a density of the plurality of sub component groups, C represents a volume percent of the plurality of sub component groups;

obtaining a regressed density according to the second measured total hydrocarbon and the predetermined relationship of density, the regressed density being summation of regressed sub densities; and obtaining an analyzing result of density according to the regressed density and the predetermined range of density.

5. The method for analyzing the liquefied petroleum gas as claimed in claim 1, further comprising:

providing a predetermined range of vapor pressure, the predetermined range of vapor pressure is based on a predetermined relationship of vapor pressure of the plurality of reference samples of the liquefied petroleum gas, the predetermined relationship of vapor pressure satisfies following condition:

a regressed sub vapor pressure=(vp'×C)/100, where vp' represents a vapor pressure of the plurality of sub component groups, C represents a volume percent of the plurality of sub component groups;

providing a predetermined range of octane number, the predetermined range of octane number is based on a predetermined relationship of octane number of the plurality of reference samples of the liquefied petroleum gas, the predetermined relationship of octane number satisfies following condition:

a regressed sub octane number=(m×C)/100, where m represents an octane number of the plurality of sub component groups, C represents the volume percent of the plurality of sub component groups;

providing a predetermined range of density, the predetermined range of density is based on a predetermined relationship of density of the plurality of reference samples of the liquefied petroleum gas, the predetermined relationship of density satisfies following condition:

a regressed sub density=(sg'×C)/100, where sg' represents a density of the plurality of sub component groups, C represents the volume percent of the plurality of sub component groups;

obtaining a regressed vapor pressure according to the second measured total hydrocarbon and the predetermined relationship of vapor pressure, the regressed vapor pressure being summation of regressed sub vapor pressures;

obtaining an analyzing result of vapor pressure according to the regressed vapor pressure and the predetermined range of vapor pressure;

obtaining a regressed octane number according to the second measured total hydrocarbon and the predetermined relationship of octane number, the regressed octane number being summation of regressed sub octane numbers;

obtaining an analyzing result of octane number according to the regressed octane number and the predetermined range of octane number;

obtaining a regressed density according to the second measured total hydrocarbon and the predetermined relationship of density, the regressed density being summation of regressed sub densities; and obtaining an analyzing result of density according to the regressed density and the predetermined range of density.

6. A device for analyzing a liquefied petroleum gas, comprising:

an inlet receiving a sample of the liquefied petroleum gas, the sample of the liquefied petroleum gas comprises a main component group, and the main component group comprises a plurality of sub component groups;

a multiposition valve, comprising an inlet end, a first outlet end, and a second outlet end, and the inlet end connecting to the inlet;

a first column connecting to the first outlet end;

a second column connecting to the second outlet end, and the second column including different separation ability from the first column;

an analyzing apparatus connecting to the first column and the second column, and the analyzing apparatus exports a first measured total hydrocarbon and a second measured total hydrocarbon, the first measured total hydrocarbon corresponds to the main component group, and the second measured total hydrocarbon corresponds to one of the plurality of sub component groups; and a computing unit configured for obtaining a regressed total hydrocarbon according to the second measured total hydrocarbon and obtaining an analyzing result of total hydrocarbon according to the first measured total hydrocarbon, the regressed total hydrocarbon, and a predetermined range of total hydrocarbon;

wherein, a predetermined relationship of total hydrocarbon and the predetermined range of total hydrocarbon are based on regression analysis of total hydrocarbon of a plurality of reference samples of the liquefied petroleum gas, the predetermined relationship of total hydrocarbon is a function of regression analysis, a plurality of variables in the function of regression analysis represent ratios of the second measured total hydrocarbon of one of the plurality of sub component groups to a summation of all the second measured total hydrocarbon of the plurality of sub component groups, and the regressed total hydrocarbon is an unknown number of the function of regression analysis, the predetermined range of total hydrocarbon is a range of a ratio of the first measured total hydrocarbon to the regressed total hydrocarbon.

7. The device for analyzing the liquefied petroleum gas as claimed in claim 6, wherein the computing unit is further configured to obtain a regressed vapor pressure according to the second measured total hydrocarbon, and to obtain an analyzing result of vapor pressure according to the regressed vapor pressure and a predetermined range of vapor pressure, the predetermined range of vapor pressure is based on a predetermined relationship of vapor pressure of the plurality of reference samples of the liquefied petroleum gas, the regressed vapor pressure is summation of a plurality of regressed sub vapor pressures, and the predetermined relationship of vapor pressure satisfies following condition:

a regressed sub vapor pressure=(vp'×C)/100, where vp' represents a vapor pressure of the plurality of sub component groups, C represents a volume percent of the plurality of sub component groups.

8. The device for analyzing the liquefied petroleum gas as claimed in claim 6, wherein the computing unit is further configured to obtain a regressed octane number according to the second measured total hydrocarbon, and to obtain an analyzing result of octane number according to the regressed octane number and a predetermined range of octane number, the predetermined range of octane number is based on a predetermined relationship of octane number of the plurality of reference samples of the liquefied petroleum gas, the regressed octane number is summation of a plurality of regressed sub octane numbers, and the predetermined relationship of octane number satisfies following condition:

a regressed sub octane number=$(m \times C)/100$, where m represents an octane number of the plurality of sub component groups, C represents a volume percent of the plurality of sub component groups.

9. The device for analyzing the liquefied petroleum gas as claimed in claim 6, wherein the computing unit is further configured to obtain a regressed density according to the second measured total hydrocarbon, and to obtain an analyzing result of density according to the regressed density and a predetermined range of density, the predetermined range of density is based on a predetermined relationship of density of the plurality of reference samples of the liquefied petroleum gas, the regressed density is summation of a plurality of regressed sub densities, and the predetermined relationship of density satisfies following condition:

a regressed sub density=$(sg' \times C)/100$, where sg' representing a density of the plurality of sub component groups, C represents a volume percent of the plurality of sub component groups.

10. The device for analyzing the liquefied petroleum gas as claimed in claim 6, wherein the computing unit is further configured to obtain a regressed vapor pressure, a regressed octane number, and a regressed density according to the second measured total hydrocarbon, and to obtain an analyzing result of vapor pressure according to the regressed vapor pressure and a predetermined range of vapor pressure, the predetermined range of vapor pressure is based on a predetermined relationship of vapor pressure of the plurality of reference samples of the liquefied petroleum gas, the regressed vapor pressure is summation of a plurality of regressed sub vapor pressures, and the predetermined relationship of vapor pressure satisfies following condition:

a regressed sub vapor pressure=$(vp' \times C)/100$, where vp' represents a vapor pressure of the plurality of sub component groups, C represents a volume percent of the plurality of sub component groups; the computing unit is further configured to obtain an analyzing result of octane number according to the regressed octane number and a predetermined range of octane number, the predetermined range of octane number is based on a predetermined relationship of octane number of the plurality of reference samples of the liquefied petroleum gas, the regressed octane number is summation of a plurality of regressed sub octane numbers, and the predetermined relationship of octane number satisfies following condition:

a regressed sub octane number=$(m \times C)/100$, where m represents an octane number of the plurality of sub component groups, C represents the volume percent of the plurality of sub component groups; and the computing unit is further configured to obtain an analyzing result of density according to the regressed density and a predetermined range of density, the predetermined range of density is based on a predetermined relationship of density of the plurality of reference samples of the liquefied petroleum gas, the regressed density is summation of a plurality of regressed sub densities, and the predetermined relationship of density satisfies following condition:

a regressed sub density=$(sg' \times C)/100$, where sg' representing a density of the plurality of sub component groups, C represents the volume percent of the plurality of sub component groups.

11. The device for analyzing the liquefied petroleum gas as claimed in claim 6, wherein the analyzing apparatus is a flame ionization detector.

* * * * *